US005469145A

United States Patent [19]
Johnson

[11] Patent Number: 5,469,145
[45] Date of Patent: Nov. 21, 1995

[54] WET DIAPER DETECTOR

[76] Inventor: Lonnie Johnson, 1640 Roswell St., Suite A, Smyrna, Ga. 30080

[21] Appl. No.: 158,612

[22] Filed: Nov. 29, 1993

Related U.S. Application Data

[63] Continuation-in-part of Ser. No. 890,162, May 29, 1992, Pat. No. 5,266,928.

[51] Int. Cl.$^6$ .................................................. G08B 21/00
[52] U.S. Cl. .......................... 340/604; 340/573; 128/886; 604/361
[58] Field of Search ..................... 340/603, 604, 340/605, 573; 200/61.05; 128/886; 604/361

[56] References Cited

U.S. PATENT DOCUMENTS

| | | | |
|---|---|---|---|
| 4,069,817 | 1/1978 | Fenole et al. | 200/61.05 X |
| 4,106,001 | 8/1978 | Mahoney | 340/604 |
| 4,754,264 | 6/1988 | Okada et al. | 340/573 |
| 4,768,023 | 8/1988 | Xie | 340/604 X |
| 4,796,014 | 1/1989 | Chia | 340/604 X |

Primary Examiner—John K. Peng
Assistant Examiner—Edward Lefkowitz
Attorney, Agent, or Firm—Kennedy & Kennedy

[57] ABSTRACT

A wet diaper detector comprises an elongated strip of material sized to be positioned in a diaper with a portion of the strip residing in a region of the diaper subject to wetness and an end of the strip protruding from the diaper at the upper rear or front portion thereof. The strip carries a pair of spaced conductors that extend along the length of the strip and terminate at the protruding end thereof. A detector and alarm assembly is adapted to be releasably coupled to the protruding end of the elongated strip and is configured to monitor the electrical resistance between the spaced conductors of the strip. When the diaper is wet by its wearer, the resistance between the spaced conductors of the strips falls below a pre-established value whereupon the detector activates the alarm to alert an attendant to change the diaper. In one embodiment, wetness is detected capacitively. When the diaper is changed, the detector and alarm assembly is decoupled from the strip for reuse and the strip is discarded along with the soiled diaper.

13 Claims, 5 Drawing Sheets

WET DIAPER DETECTOR

REFERENCE TO RELATED APPLICATION

This application is a continuation-in-part of U.S. patent application Ser. No. 07/890,162 filed May 29, 1992, now U.S. Pat. No. 5,266,928.

FIELD OF THE INVENTION

This invention relates generally to moisture sensing devices and more particularly to a wet diaper detector assembly for alerting parents or attendants to the presence of wetness in an infant's diapers or undergarments.

BACKGROUND OF THE INVENTION

Baby diaper rash is for the nursing mother one of the most enigmatic problems of infant rearing. One of the primary causes of such diaper rash is, of course, that babies frequently wet their diapers and wear the wet diapers for prolonged periods before they are changed. While a few babies tend to cry when wet, many babies do not cry, and the mothers of this latter group of babies are not alerted to the wet diaper condition until the diaper has been worn for a time sufficient to cause diaper rash.

In an effort to reduce the time during which wet diapers are in contact with a baby's skin, mothers often adhere to a specific change of diaper schedule wherein a baby's diapers are changed periodically according to a pre-established timetable. Although such diaper-changing schedules are helpful, a real reduction of time during which urine contacts the baby's skin is not often realized because no prescribed time table can anticipate an individual baby's changeable physical constitution. For example, an infant might wet its diaper immediately after a scheduled change of the diaper and thus, unknown to the mother, be left in a soiled diaper until the next scheduled change of the diaper.

Alarm devices have previously been proposed as a means for informing a parent or attendant that a wet diaper condition has occurred so that the baby's clothing can be changed and its skin cleansed to eliminate the urine/skin contact and reduce the chances of diaper rash. One example of such a proposed alarm device is disclosed in U.S. Pat. No. 3,460,123 of Bass. Bass shows a wet garment alarm system that includes a transmitter for producing a radio signal and a diaper formed with a pair of spaced conductive screens having an electrolyte disposed therebetween. The transmitter is electrically coupled to the screens and adapted to produce a radio signal when the resistance between the screens falls below a predetermined level. In use, the transmitter of Bass is secured to the upper waist portion of an infant's diaper, and the diaper is secured to its wearer with the pair of conductive screens positioned at the crotch portion of the diaper. When the diaper is wet by the wearer, urine flows into the crotch portion of the diaper and electrically bridges the space between the conductive screens thus reducing the resistance between the screens. This reduced resistance, in turn, actuates the transmitter to produce a radio signal for activating a remote alarm to alert a parent or attendant to the wet diaper condition.

Another system for detecting and signaling a wet diaper condition is disclosed in U.S. Pat. No. 4,106,001 of Mahoney, wherein a garment clip houses a moisture detector and alarm. The garment clip is adapted to be clipped onto an exposed edge of a diaper or other garment to be monitored. An elongated strip of material is detachably connected at one end to the clip and is sized to be positioned in a region of the diaper subject to wetness such as, for example, the crotch region. The strip of material includes a pair of embedded spaced electrodes that are coupled to the detector/alarm. When moisture is provided by the wearer of the undergarment, a partial short circuit occurs between the electrodes at some point along the strip of material. This short circuit is detected by the moisture detector, which activates the alarm to provide an audible indication of urination by the infant or wearer.

A similar system is disclosed in U.S. Pat. No. 4,796,014 of Chia, wherein a safety pin with spaced electrical conductors is coupled to a detector and alarm device attached to a diaper. When urine bridges the space between the electrical conductors of the safety pin, a detection circuit is completed, which, in turn, activates the alarm. The Chia device further includes a time delay circuit to ensure that the alarm does not interfere with an infant's normal urination cycle.

While these and similar devices have been somewhat successful in signaling a wet diaper condition, they still tend to exhibit numerous problems and shortcomings inherent in their respective designs. For instance, several of these devices include a pair of conductive electrodes built into the material forming the diaper itself. Such a configuration is shown in the patent of Bass. Obviously, manufacture of these types of diapers can be relatively expensive since special diaper forming machinery must be developed and implemented. Another common problem with prior art devices is that the detecting strips that reside in the diaper are configured as integral non-detachable elements of the detector and alarm circuits. With such a configuration, the entire device often must be discarded when the sensing strip becomes worn, which is inefficient and wasteful. Also, manufacturing the detection devices and alarms in some prior art devices can become complicated and costly. Finally, the mere fact that conductive electrodes must extend into the diaper to detect resistive changes when a baby wets is objectionable to many parents and, under the proper condition, could result in a mild shock to an infant wearer.

Accordingly, there exists a continuing and heretofore unaddressed need for a wet diaper detector and alarm system that is usable with a conventional disposable or non-disposable diaper, is inexpensive to produce, easy and convenient to use, does not necessarily require that conductive electrodes extend into the diaper itself, and that does not require expensive and bulky housings that must be secured to a wearer's garments. It is to the provision of such a wet diaper detector and alarm system that the present invention is primarily directed.

SUMMARY OF THE INVENTION

Briefly described, the present invention comprises a wet diaper detector and alarm system for use with conventional undergarments or diapers to alert a parent or attendant to a wet diaper condition and also to provide a dependable manner by which young children can be toilet trained. In one preferred embodiment, the wet diaper detector and alarm system of this invention comprises an elongated strip of generally absorbent material having a pair of spaced embedded conductors extending therealong. The conductor bearing strip is sized to be positioned and secured in a diaper extending through a wetness prone region thereof with one end of the strip protruding from the diaper, preferably at the front or rear waistband portion thereof. A generally rectangular flexible band supports miniaturized electronic detection and alarm circuitry and is configured to be removably attached to the protruding end of a conductor bearing strip that previously has been secured in the diaper. The band includes a pair of electrical contacts that are coupled to the detection circuit of the band with each contact being configured to become electrically coupled to a respective one of the conductors of the elongated strip when the band is removably attached to the strip end. With the band thus attached to the protruding end of a conductor bearing strip, the band and strip end can be removably mounted to the exterior of the diaper with a rectangular adhesive backed patch that covers and protects the band during use.

The electronic detector and alarm of the present invention is configured to monitor the resistance between the spaced conductors of an attached conductor bearing strip and to trigger the alarm, which preferably emits a pleasant audible melody, when such resistance falls below a pre-established threshold. When the system is properly secured to an infant's diaper as described above, the electrical resistance between the two electrical conductors of the elongated strip normally remains above the pre-established threshold when the diaper is dry. However, when the wearer wets its diaper, the resulting moisture permeates the strip therein and causes the resistance between the two conductors of the strip to fall below the pre-established threshold. As a result, the detector triggers the audible alarm to alert an adult or attendant immediately of the wet diaper condition so that the diaper can be changed.

In another embodiment of the invention, a T-shaped strip of material is adapted to be secured to a diaper with its shorter leg positioned on the outside of the diaper at the upper front or rear portion thereof and with its longer leg extending therefrom into the diaper and through the crotch area thereof. A pair of spaced conductors are disposed along the length of the longer leg and each conductor terminates in a contact at the intersection of the legs of the T-shaped strip, which normally lies on the outside of the diaper. A miniaturized detector and alarm circuit is contained within a small plastic housing having a pair of spaced external contacts positioned to engage the contacts at the strip intersection when the housing is located on the T-shaped strip at the intersection of its legs.

In use, the T-shaped strip of this second embodiment is placed in a diaper as described and the detector/alarm housing positioned at the intersection of the strip's legs with its contacts engaging the contacts of the strip. The shorter leg of the T-shaped strip, which preferably bears adhesive, is then folded up over the housing and adhesively attached to the front of the diaper to secure the detector in place. The circuitry then functions in the same way as with the previously described embodiment to signal a wet diaper condition. When a wet diaper is changed, the small detector housing is simply removed and reused while the used, inexpensive T-shaped strip is discarded with the soiled diaper.

In a third embodiment of the invention, the electronic detection and alarm circuit is housed in a small plastic button-shaped housing. The back side of the housing is provided with two conductors shaped with interleaved fingers to form a parallel plate-type capacitor that functions as a detector. The circuit includes an oscillator coupled through the capacitor detector to an amplification, rectification, and comparison circuit. In use, the button is removably fixed to the outside of a diaper adjacent a wetness prone region thereof. As long as the diaper is dry inside, the capacitive coupling between the fingers of the detector is weak and a relatively small percentage of the oscillating signal is transmitted across the capacitor. When amplified and rectified, this small signal is less than a predetermined threshold and the comparison circuit does not activate the alarm. However, when the baby wets, the urine acts as an electrolyte that significantly enhances the capacitive coupling between the finger plates of the capacitor detector. Thus, substantially more of the oscillator signal is transmitted and, when amplified and rectified, generates a signal greater than the pre-established threshold. In response, the comparison circuit activates the audible alarm signaling a wet condition. Once a diaper has been wet, the detector button is removed for reuse on a new diaper.

Thus, it is seen that an improved wet diaper detector and alarm system is now provided for detecting and signaling a wet diaper condition quickly, reliably, economically, and conveniently. The components of the system are designed so that the more expensive elements, i.e. the electronic detection and alarm circuitry, are easily removed and reused while the inexpensive conductive strip, which becomes soiled along with the diaper, is simply discarded. The system is thus highly efficient relative to prior art systems. Also, in the capacitively coupled embodiment, there are no conductive strips or any other elements that extend into the diaper itself.

The present invention provides great advantages in the care of wetting infants since it allows a wet diaper to be changed immediately, thus reducing greatly instances of urine induced diaper rash. The system is further advantageous in the toilet training of infants since its alarm can signal a parent or attendant to take the infant to a toilet immediately upon commencement of wetting. In this way, the child makes the mental connection between wetting and the toilet much quicker than with older fashioned toilet training techniques. These and other features, objects and advantages of the invention will become more apparent upon review of the following detailed description taken in conjunction with the accompanying drawings.

DETAILED DESCRIPTION OF THE PREFERRED EMBODIMENTS

Figure 1:
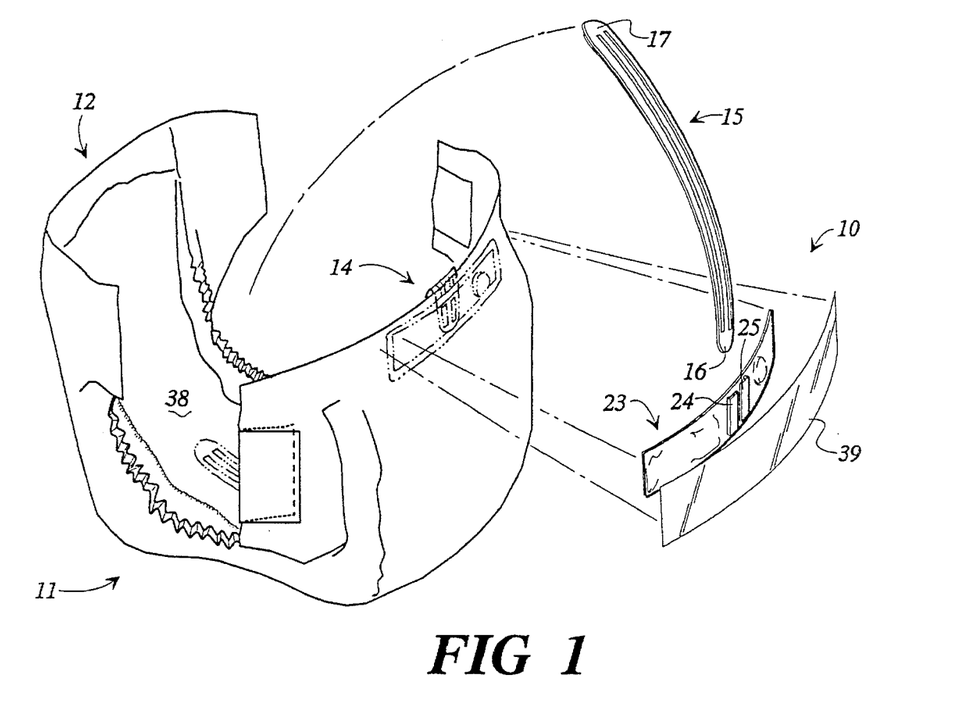
FIG. 1 is a perspective partially exploded view of a wet diaper detector that embodies principles of the present invention in one preferred form.

Referring now in more detail to the drawings, in which like numerals refer to like parts throughout the several views, FIG. 1 illustrates a wet diaper detector assembly 10 that embodies principles of the invention in one preferred form. The assembly 10 is shown partially exploded to reveal clearly the elements of the invention with the preferred placement of the assembly on a diaper 11 being illustrated in phantom lines.

Figure 2:
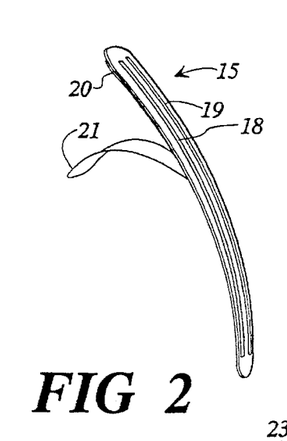
FIG. 2 is a detailed perspective view of the disposable conductor bearing strip of the invention.

The detector assembly 10 comprises an elongated strip of material 15, which has first and second ends 16 and 17 respectively. The strip 15 preferably is formed of a moisture absorbent insulating material and carries a pair of spaced conductors 18 and 19 (FIG. 2) that extend along the length of the strip 15. As illustrated in FIG. 2, the strip 15 is provided with an adhesive backing 20 that is normally protected by a peel-off strip 21. In use, the peel-off strip 21 is removed just prior to attaching the assembly 10 to a diaper so that the strip 15 can be adhered securely within the diaper extending through the crotch area thereof as illustrated in phantom lines in FIG. 1.

A generally rectangular flexible band 23 carries the electronic detector and alarm circuitry of the invention and is adapted to be positioned on the exterior of a diaper 11 at the upper front or rear portion 14 thereof. In use, the band 23 is releasably secured to the diaper by means of a rectangular adhesive patch 39 that is slightly larger than the band 23 and that is applied over the band to cover and protect it and to secure it releasably to the diaper's exterior surface.

Figure 3:
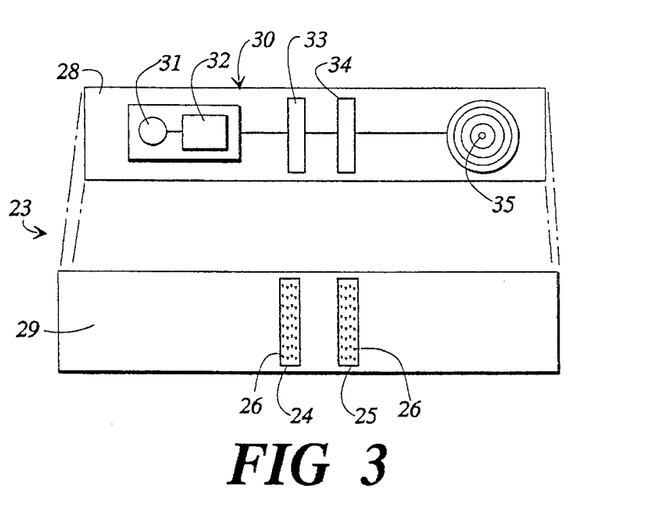
FIG. 3 is a partially exploded view showing a preferred construction of the rectangular component carrying band of the invention.

As best illustrated in FIG. 3, the flexible band 23 preferably is fabricated from two rectangular strips 28 and 29 of flexible material between which is sandwiched the miniaturized electronic components 30 of the invention. During assembly, the rectangular strips 28 and 29 are adhesively and permanently joined to form a unitary assembly such that the electronic components become sealed and protected between the strips 28 and 29.

The electronic components 30 and their configuration are discussed in detail hereinbelow. In general, however, these components comprise a power source in the form of a small thin watch battery 31 that powers a detector circuit 32 and an audible alarm 35, which, in the preferred embodiment, comprises a miniaturized melody source of the type commonly embedded within greeting cards and the like. A pair of spaced electrical contacts 33 and 34 are positioned in the mid-portion of the band 23 and are coupled to the detector 32. The detector 32 is configured to monitor the electrical resistance between the contacts 33 and 34 and to activate the alarm 35 when such resistance falls below a pre-established value.

The exterior surface of rectangular strip 29 carries a pair of spaced spiked or barbed conductive guides 24 and 25 positioned to overly and make electrical contact with the contacts 33 and 34 when the strips 28 and 29 are sandwiched together. The guides 24 and 25 are configured to receive and position the protruding end 16 of strip 15 at the mid-portion of band 23 as illustrated in FIG. 1. The spikes or barbs 26 penetrate the strip and make electrical contact between each of the guides 24 and 25 and a respective one of the conductors 18, 19 of the strip 15. It will thus be clear that, with the wet diaper detector thus assembled, the detector circuit monitors the electrical resistance between the spaced conductors of the strip 15.

When using the embodiment of FIGS. 1–3 for detecting and signaling a wet diaper condition, the elongated conductor bearing strip 15 is adhesively secured within a diaper extending through the crotch area thereof with one end 16 of the strip protruding from within the diaper at the upper edge 14 thereof. The detector band 23 is then pressed onto the strip end 16 with each conductor of the strip overlying a respective one of the barbed guides 24 and 25. The pressing of the strip end and band together causes the barbs 26 to penetrate the strip to establish reliable electrical contact between the guides 24 and 25 and the conductors 18 and 19.

With the strip end and band pressed together, the strip is folded over the top edge of the diaper to position the detector band on the outside of the diaper of the upper front or rear portion thereof as shown in phantom lines in FIG. 1. The band 23 and strip end 16 are then securely but releasably affixed to the diaper by means of the adhesive backed patch 39, which is sized to overly and cover the band to protect it from food, moisture, and unwanted tampering.

With the assembly 10 thus installed, the diaper is placed on an infant in the usual way and the detector circuit begins to monitor the resistance between the conductors 18 and 19 within the diaper. The pre-established resistance threshold value is selected such that the monitored resistance between the conductor is above the threshold when the diaper is dry but falls below the threshold when the diaper and the strip therein become wet. Accordingly, when the infant wets its diaper, the resulting resistance drop is detected by the detector, which, in turn, activates the alarm to alert a parent or attendant to the wet diaper condition. When the soiled diaper is changed, the detector band 23 is removed from the diaper and decoupled from the strip end 16 for reuse on a fresh diaper. The used conductor strip 15, which is inexpensive and thus expendable, is simply discarded with the soiled diaper.

Figure 4:
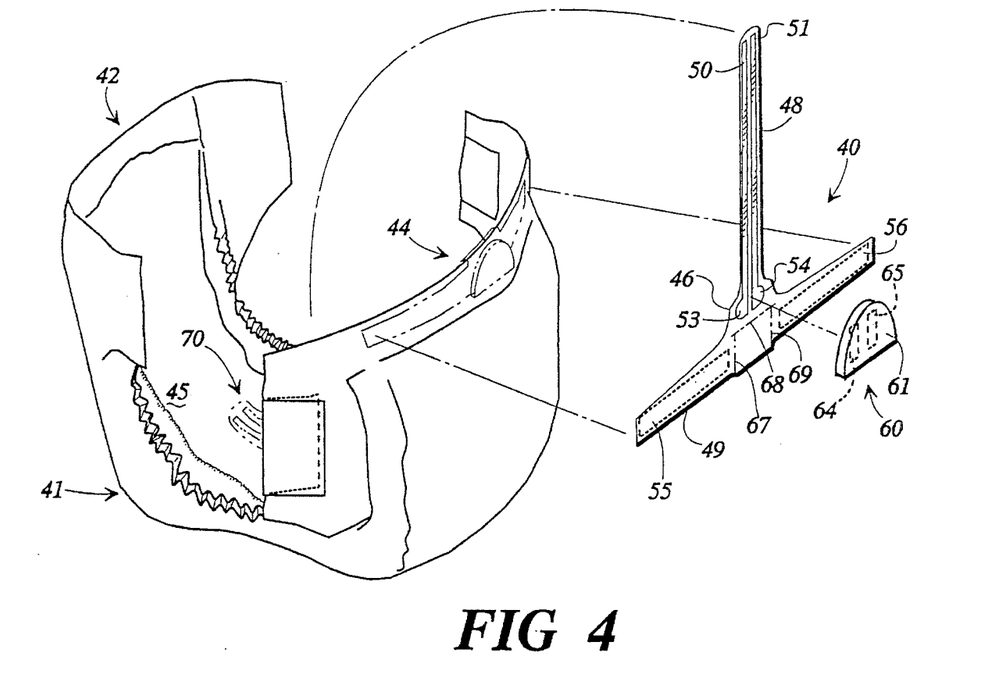
FIG. 4 is a perspective partially exploded view showing an alternate embodiment of the wet diaper detector of the present invention.
Figure 5:
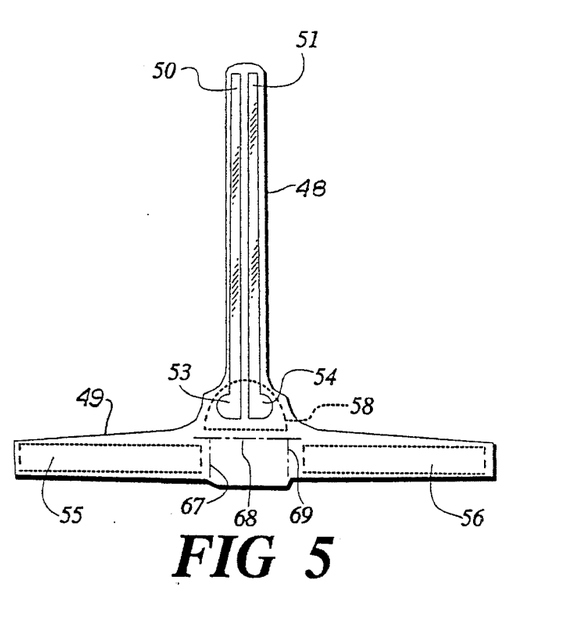
FIG. 5 is a top plan view of the disposable T-shaped strip of the embodiment shown in FIG. 4.
Figure 6:
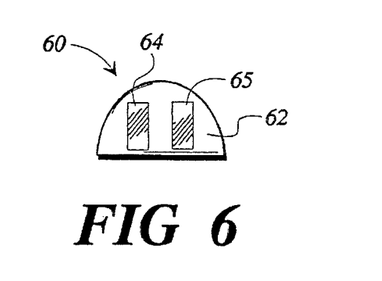
FIG. 6 is a rear view showing a preferred configuration of the detector and alarm module of the embodiment shown in FIG. 4.

FIGS. 4–6 illustrate a second or alternate embodiment 40 of the present invention. This embodiment is also configured for use with an ordinary diaper 41 that has front and rear portions 42 and 44 and an inner intermediate portion 45. The assembly 40 comprises an inverted T-shaped flexible strip 46 having an elongated first leg 48 and a second leg 49, which preferably extends normal to the first leg 48 (FIGS. 1 and 2). Extending along the length of the first leg 48 is a pair of spaced conductors 50 and 51, that terminate in respective contacts 53 and 54 at the intersection of the legs of the T-shaped strip 46.

Preferably, adhesive backings 55 and 56 are provided on the second leg 49 of the T-shaped strip 46 for purposes detailed below and the backings are normally protected by peel-off strips (not shown). Adhesive backing and a peel-off strip also is provided along the back side of leg 48 so that this leg can be secured within the interior of the diaper as detailed below. An adhesive backing 58 (FIG. 5) can also be provided on the back of the T-shaped strip 46 at the intersection of its legs for securing the wet diaper detector assembly 40 onto the exterior surface of the diaper 41 as illustrated in phantom lines in FIG. 4.

Figure 7:
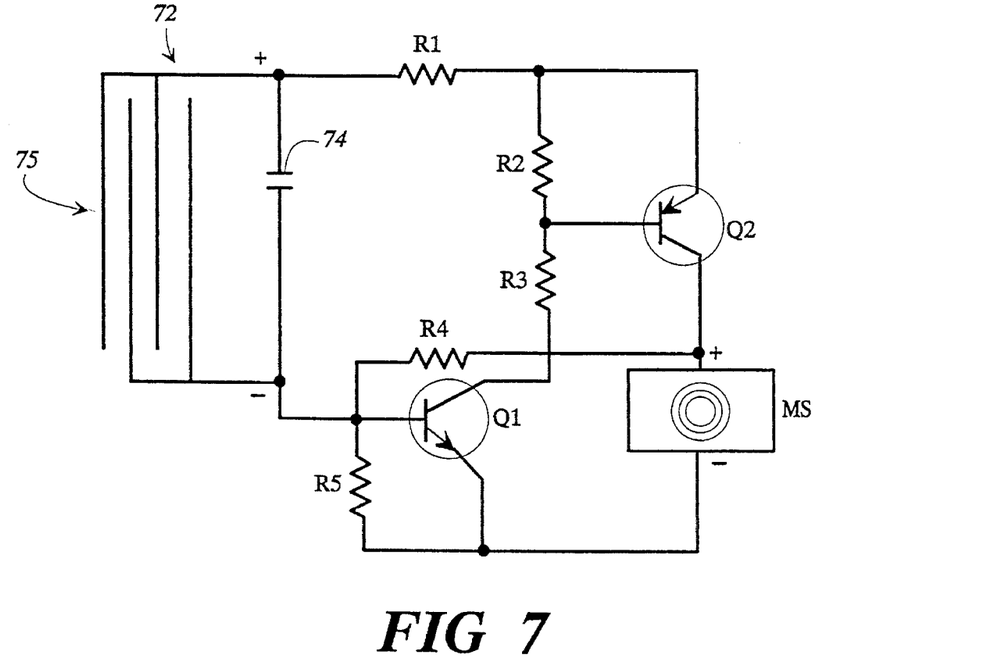
FIG. 7 is an electrical schematic diagram showing one preferred circuit for implementing the present invention.
Figure 8:
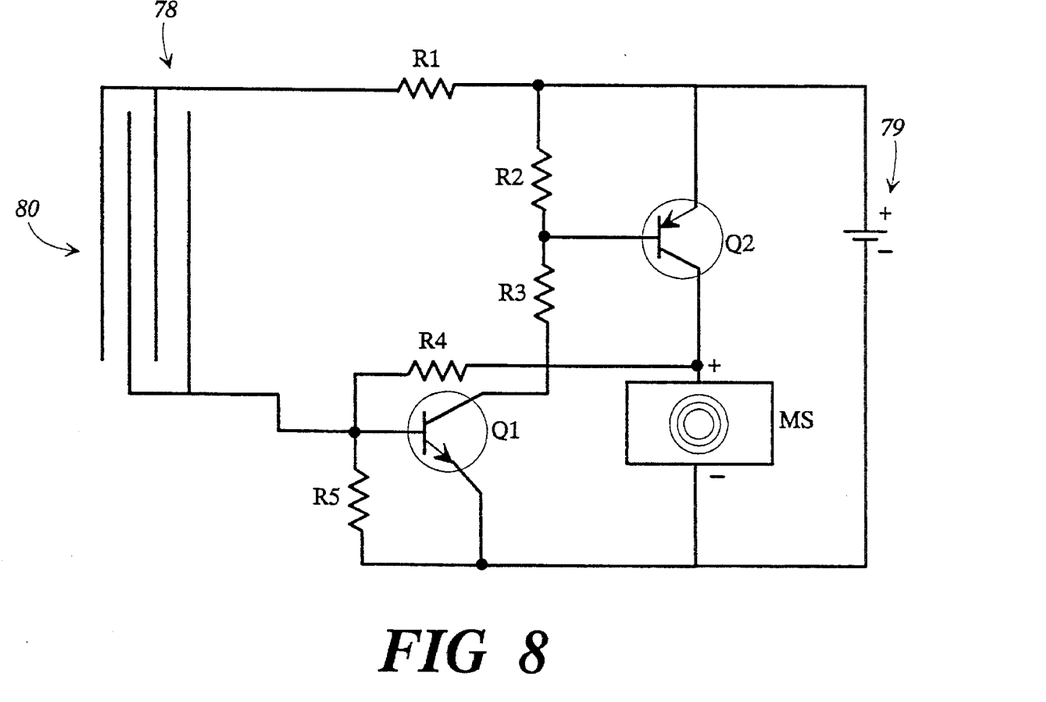
FIG. 8 is an electrical schematic diagram showing an alternate circuit for implementing the invention.

As illustrated in FIG. 6, a detector and alarm circuit is encased within a thin plastic housing 60 having a front side 61 (FIG. 4) and a rear side 62. A pair of spaced electrical contacts 64 and 65 are located on the rear side 62 of the housing 60 and are electrically coupled to the detector circuit within the housing, as discussed below and as illustrated in FIGS. 7 and 8.

The housing 60 encloses the miniaturized electrical circuitry that, as in the first embodiment, monitors the electrical resistance between the contacts 64 and 65 and activates the alarm when such resistance falls below a pre-established threshold value. The contacts 64 and 65 are spaced to overlay and make electrical contact with the contacts 53 and 54 on the T-shaped strip 46 when the housing 60 is pressed into position at the intersection of the legs of the strip as best seen in FIG. 4. It will be apparent that with the housing 60 thus positioned, the detector monitors the electrical resistance between the spaced conductive strips 50 and 51 that extend along leg 48 and activates the alarm when such resistance falls below the pre-established threshold value.

The wet diaper detector assembly 40 is shown in phantom lines in FIG. 4 as it appears when installed on a diaper 41 for use. When installing the assembly, the T-shaped strip 46 is first affixed to the outside rear or front portion 44 of the diaper by means of the adhesive backing 58 on the back side of the strip 46. The second leg 48 of the strip 40 is then folded over the top edge of and into the interior of the diaper, where it is adhesively secured in position extending through the crotch area of the diaper (FIG. 4). Thus, the conductive strips 50 and 51 are exposed within the diaper at its crotch portion, which tends to be the portion most susceptible to wetness.

With the first leg 48 of the T-shaped strip positioned in the diaper as shown at 70, the detector housing 60 is positioned at the intersection of the legs of the T-shaped strip with each of its contacts 64 and 65 engaging a respective one of the contacts 53 and 54 thus coupling the detector to the conductors 50 and 51. The protective peel-off strips are then removed from the adhesive backing 55 and 56 and the second leg 49 of the strip 46 is folded up and over the housing 60 and adhesively secured to the exterior of the diaper on either side of the housing. The housing 60 is thus securely captured and held in place by the folded and secured second leg 49 of the T-shaped strip 46 as illustrated in FIG. 4. With the detector assembly 40 thus secured, the diaper can be fitted to an infant or toddler in the normal way.

When the diaper 41 is fitted to the infant, the resistance between the two metal strips 50 and 51 normally remains above a threshold as long as the interior portion 45 of the diaper 41 is dry. However, when the infant wets his diaper, thus wetting the first leg 48 of the T-shaped strip 46 at 70, the resulting moisture causes the resistance between the conductors 50 and 51 to fall below the threshold level. The detector circuit detects this reduction in resistance and activates the alarm, which preferably emits a pleasant melody, to alert an adult or an attendant of the wet diaper condition. The wet diaper can then be changed, whereupon the detector housing 60 is removed for reuse while the used T-shaped strip 46 is discarded along with the soiled diaper.

FIG. 7 is an electronic schematic diagram illustrating a preferred circuit for implementing the present invention. In this embodiment, the spaced conductors 75, which normally are positioned on the strip within a diaper, are formed of dissimilar metals such as, for example, silver and copper. In this way, when acidic urine contacts the conductors the urine functions as an electrolyte and the conductors and urine become a battery that supplies power for operation of the circuit.

As the conductors 75 become charged upon contact with urine, they provide current to charge capacitor 74. When capacitor 74 becomes sufficiently charged, the electrical potential across the capacitor functions to "turn on" transistor Q1, which, in turn, conducts sufficient current through R1 and through voltage divider pair R2 and R3 to turn on transistor Q2. With transistor Q2 in its on or conducting state, power is supplied to the alarm MS, causing the alarm to emit an audible alert signal. Preferably, the alert signal is a pleasing melody that will not upset an infant but that will be sufficiently noticeable to alert a parent or guardian to the presence of wetness within the diaper. In some instances, sufficient current is supplied by the urine battery for continuous operation of the alarm. However, in some instances, the generated current is not sufficient and the alarm is sounded intermittently as the capacitor 74 charges and discharges.

FIG. 8 is an electronic schematic diagram illustrating another embodiment of a detector and alarm circuit for implementing the present invention. In this embodiment, the circuit is powered by an auxiliary battery 79. In operation, the electrical resistance between conductors 80 falls when the conductors are contacted with urine or other wetness in the diaper. In turn, current is conducted through resistor R5 and R1. The resulting voltage drop across resistor R5 turns transistor Q1 on, which, in turn, turns on transistor Q2 as with the embodiment of FIG. 7. With transistor Q2 in its on or conducting configuration, power is supplied to the alarm MS, which emits an audible signal to alert the attendant of the wet condition of the diaper. With this embodiment, the audible alarm sounds continuously until the wet diaper is changed since continuous power is supplied by the battery 69.

FIGS. 9–13 illustrate another preferred embodiment of the present invention wherein wetness within the diaper is detected through capacitive rather than resistive coupling. In this embodiment, there are no strips or conductors that extend into the interior portion of the diaper. Rather, the detector and alarm circuit is contained in a button-shaped housing that is fixed completely on the exterior of the diaper.

Figures 9, 10:
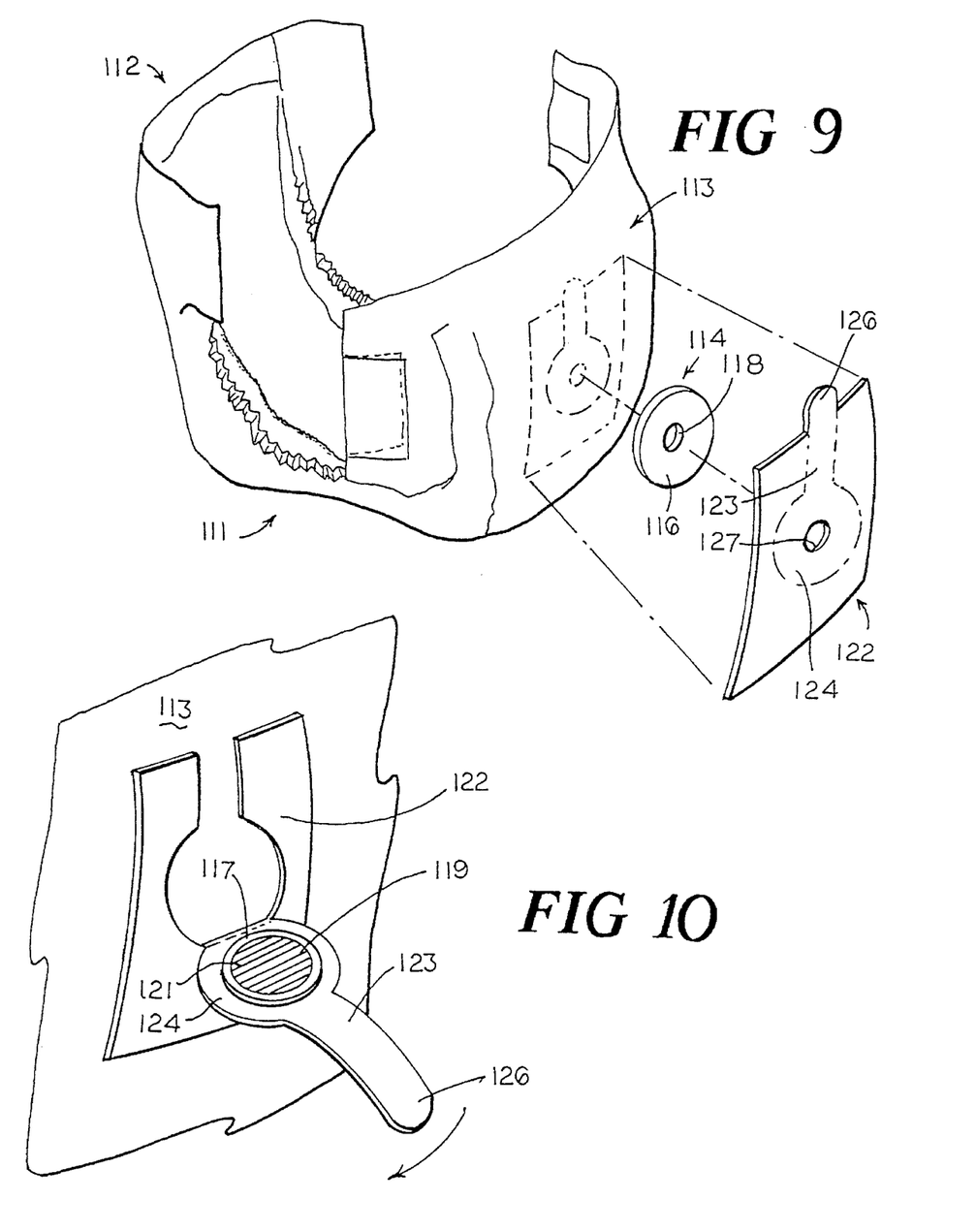
FIG. 9 is a perspective view illustrating a preferred method of releasably fixing the third, capacitively coupled, embodiment of the invention to a diaper.
FIG. 10 illustrates the removal of the embodiment of FIG. 9 from a soiled diaper for reuse on a new diaper.

Referring to FIGS. 9 and 10, the diaper 111 is seen to have a back side 112 and a front side 113. While the illustrated diaper is of common disposable construction, it will be obvious that this embodiment of the invention might well be used with virtually any type of infant diaper. As best seen in FIG. 9, the detector and alarm circuitry in this embodiment is contained within a button-shaped housing 114 having a front surface 116 and a rear surface 117 (FIG. 10). The front surface 116 of the housing 114 is provided with a small central opening 118 through which the audible signal produced when a diaper is wet is emitted. The rear surface 117 of the housing is provided with a pair of electrical conductors 119 and 121 (best seen in FIG. 13). The conductors 119 and 121 are formed with mutually interleaved fingers that together define what is essentially a parallel plate capacitor. Thus, the conductor 119 is capacitively coupled to the conductor 121, as more fully described below.

The detector and alarm circuit of this embodiment of the invention preferably is removably fixed to the front surface or crotch area of a diaper 111 by means of an adhesive patch 122. The patch 122 has a peel-away backing (not shown) that can be removed to expose adhesive on the back surface of the patch. The adhesive patch 122 is formed with a generally key-shaped tear-away tab 123. The tab 123 has a circular bulb portion 124, which is positioned approximately in the center of the patch 122 and is slightly larger in diameter than the detector and alarm housing 114. The tab 123 is also formed with a finger 126 that extends upwardly beyond the top edge of the patch 122. It will be understood that the back side of the patch 122 is provided with adhesive in all regions except the region defined by the tab 123 so that the tab itself does not stick to the surface of the diaper when the patch is adhered to the diaper.

In use, the peel-away backing is removed from the adhesive patch 122 and the patch is secured to the outside surface of the diaper as shown in FIG. 9 with the detector and alarm housing 114 sandwiched between the patch 122 and the surface of the diaper and positioned behind the bulb portion 124 of the tear-away tab 123. For this purpose, the bulb portion 124 of the tab is provided with a cut-out opening 127 through which the audible signal emitted from the detector can be emitted.

With the housing 114 thus fixed to the surface of the diaper, it will be understood that the rear surface 117 and capacitively coupled conductors 119 and 121 are held firmly against the outside surface of the diaper. As described in more detail below, when the interior of the diaper is dry, the conductors are only weakly capacitively coupled. However, when the diaper becomes wet inside, the moisture within the diaper acts as an electrolyte that increases the capacitive coupling between the conductors 119 and 121. This increased capacitive coupling is sensed by the circuit of this embodiment and an audible alarm is triggered in response thereto to alert a parent that its infant's diaper has been wet. As shown in FIG. 10, when the wet diaper is changed, the finger 126 of the tab 123 is grasped firmly and the tear-away tab 123 is pulled downwardly away from the patch 122 as indicated by the arrow in FIG. 10. This allows the detector housing 114 to be removed from the diaper so that it can be applied to a new dry diaper for continued wetness monitoring. Thus, this embodiment of the invention not only eliminates the need for interior conductors in the diaper, it is also easily removed and reused many times with only the inexpensive patch 122 being discarded with each use.

Figure 11:
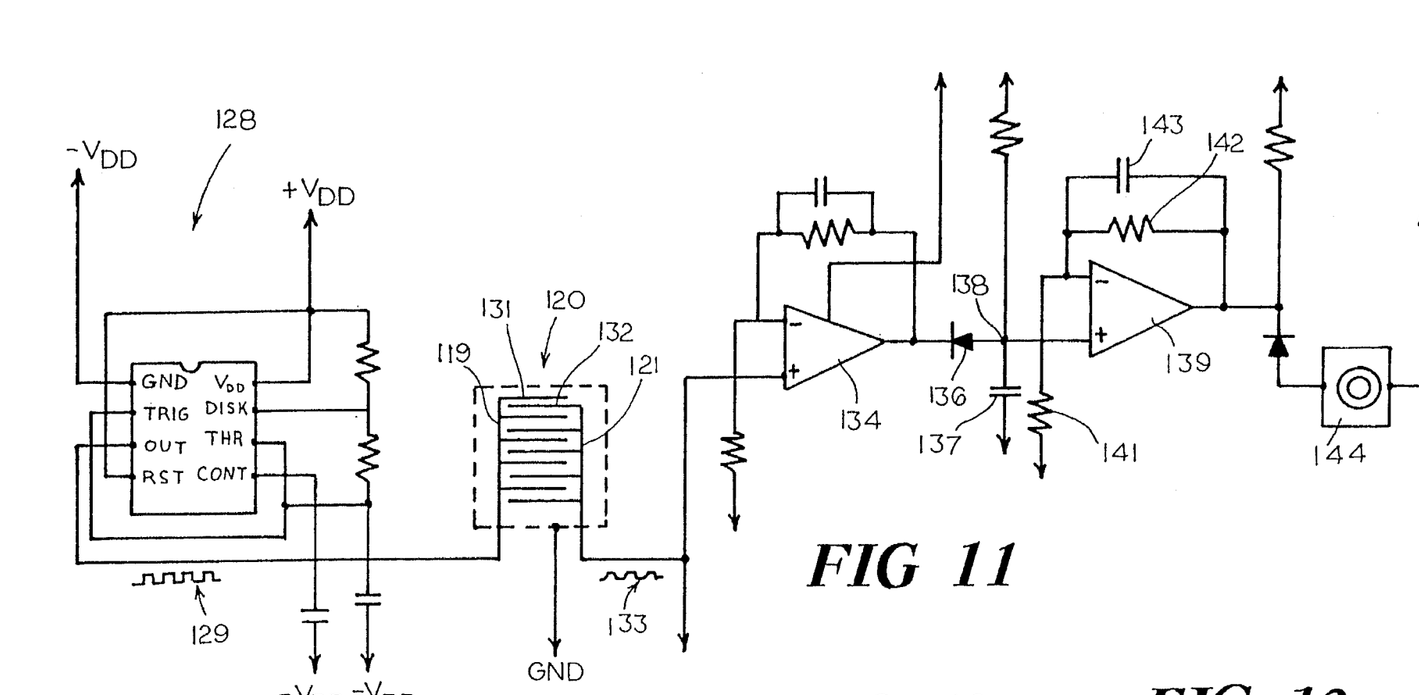
FIG. 11 is an electronic schematic showing a preferred circuit for implementing the third, capacitively coupled, embodiment of the invention.

FIG. 11 illustrates a preferred electronic circuit for implementing the capacitively coupled embodiment of the present invention. In this embodiment, an oscillator 128 is configured to provide an oscillating voltage signal at its output. In the preferred embodiment, the oscillator 128 comprises an electronic timer chip, such as a Model 555 or 551 chip, that is configured to oscillate at a predetermined frequency to provide a generally square wave output. There are many other circuits that could be configured to provide an oscillating signal for use in the present invention. However, the configured timer chip of the illustrated embodiment is considered preferable because it is inexpensive and easily configured. However, this should not be considered to be a limitation of the present invention since any other means of producing an oscillating voltage signal would function equally well in the present invention. Whatever the configuration of the oscillator 128, it is essential that it produce an oscillating voltage signal such as that illustrated at reference numeral 129 in FIG. 11.

As discussed above, the capacitive sensor 121, which is disposed on the rear surface of the housing 114, comprises a first conductor 119 and a second conductor 121. The conductors 119 and 121 are configured to have interleaving fingers 131 and 132. This configuration of the conductors 119 and 129 creates what essentially is a parallel plate capacitor so that the conductor 119 is capacitively coupled to the conductor 121. Thus, when the oscillating voltage signal 129 is applied to the conductor 119, the signal is capacitively transmitted to the conductor 121 with an efficiency that depends upon the spacing between the fingers and the dielectric properties of the medium in the region of the fingers. At any rate, some portion of the signal 129 is capacitively transmitted to the conductor 121 and this transmitted signal is represented by number 133 in FIG. 11.

The capacitively transmitted signal 133 is fed to the input of a first operational amplifier (op. amp.) 134, which is configured as a simple signal amplifier. The amplified signal present at the output of op. amp. 134 is rectified and smoothed by means of a diode 136 in conjunction with a capacitor 137 to produce a DC voltage that is proportional in value to the amplitude of the signal 133 transmitted through the sensor 120. Thus, when more of the signal 129 is transmitted through the sensor, the DC voltage at junction 138 decreases proportionally.

The DC voltage at junction 138 is fed to the input of a second op. amp. 139, which, in this instance, is configured as a simple comparator. The DC voltage at 138 is compared by op. amp. 139 to a pre-established threshold voltage that is determined by the values of resistors 141 and 142 and capacitor 143. As long as the DC voltage at 138 remains above the threshold voltage, the output of op. amp. 139 is high. However, if the DC voltage at 138 rises below the established threshold voltage, the output of op. amp. 139 goes low. Finally, the output of op. amp. 139 is coupled to a beeper 144 in such a way that when the output of op. amp. 139 goes low, the beeper 144 is activated to sound an audible alarm.

The just described circuit functions as follows. The sensor 120 is held firmly against the exterior surface of a diaper in a region of the diaper subject to wetness. As long as the diaper is dry, the capacitive coupling between the conductors 119 and 121 is relatively small so that a relatively small portion of the signal 129 is transmitted through the sensor 120. However, when the diaper becomes wet, the urine in the diaper functions as an electrolyte which increases the efficiency of capacitive coupling between the conductor 119 and 121. As a result, more of the signal 129 is capacitively transmitted through the sensor 120 and the amplitude of the transmitted signal 133 increases. This increased amplitude signal is amplified by op. amp. 134 and rectified by diode 136 and capacitor 137 so that the DC voltage present at 138 decreases in proportion to the increased amplitude of signal 133. In practice, the values of resistors 141 and 142 and capacitor 143 are selected to establish a threshold voltage that is between a typical DC voltage at 138 when the diaper is dry and a typical DC voltage at 138 when the diaper is wet. Thus, when the voltage at 138 increases as a result of a wet diaper, the threshold voltage of op. amp. 139 is exceeded. This causes the output of op. amp. 139 to go low which, in turn, activates the audible beeper 144 to alert a mother that its baby's diaper has become wet. The wet diaper can then be changed and the housing 114 removed and used on a new diaper as discussed above.

Figure 12:
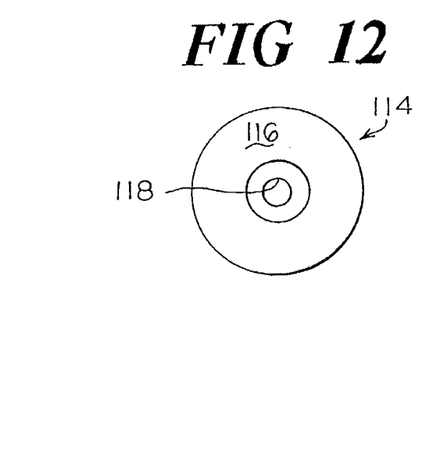
FIG. 12 is a front plan view of the button-shaped housing for the third embodiment of the present invention.
Figure 13:
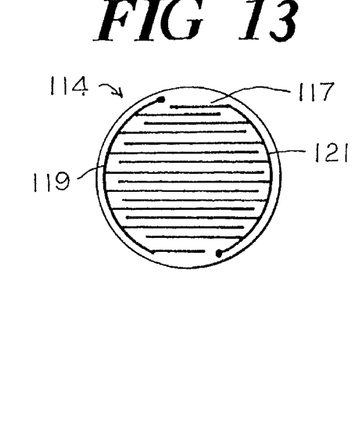
FIG. 13 is a rear plan view of the third embodiment showing the interleaved fingers of the capacitor detector.

FIGS. 12 and 13 show a preferred embodiment of the front and rear surfaces of the detector housing 114 respectively. As can be seen, the front surface 116 of the housing is provided with an opening 118, through which the audible beep signal is transmitted when a diaper is wet. The rear surface 117 of the housing 114 carries the conductors 119 and 121 with their interleaved fingers 131 and 132 positioned as shown. While the particular configurations shown in FIGS. 12 and 13 are preferred, it will be understood that such configurations are not a requirement nor a limitation but are only shown as exemplary configurations.

The invention has been disclosed and described herein in terms of preferred configurations and methodologies. However, it will be obvious to those of skill in the art that numerous variations of the illustrated embodiments could be implemented within the scope of the invention. For example, the audible alarm of the preferred embodiments might easily be replaced with a visual indicator, such as a flashing LED, or even a small transmitter for transmitting a radio signal to a remote receiver when the diaper becomes wet. Further, a wide variety of simple electronics in addition to those illustrated might be implemented to perform the same functions in an acceptable way. These and other additions, deletions, and modifications might well be made to the exemplary embodiments illustrated herein without departing from the spirit and scope of the invention as set forth in the claims.

I claim:

1. An apparatus for use with a diaper to detect the occurrence of a wet condition in the diaper and produce an alarm signal in response to such detection, said apparatus comprising:

a housing having a front surface and a rear surface and being sized to contain electronic components and to be affixed to the exterior surface of a diaper with said rear surface of said housing positioned against the diaper's exterior surface;

capacitive sensor means located on said rear surface of said housing, said sensor means having a first conductor capacitively coupled to a second conductor, said capacitive sensor means being configured and positioned on said housing rear surface to be positioned against the exterior surface of the diaper when said housing is affixed to the diaper with no portion of said capacitive sensor means extending into the interior of the diaper;

circuit means in said housing for monitoring the electrical capacitance between said first conductor and said second conductor of said capacitive sensor means;

means for producing an electrical signal when the electrical capacitance between said first conductor and said second conductor meets a pre-established criteria;

means responsive to said electrical signal for producing an alarm; and means for removably affixing said housing to the exterior surface of the diaper with said capacitive sensor means held against the diaper, whereby the capacitance between the first and second conductors increases as a result of the dielectric effects of a wetted diaper and the increased capacitance triggers an alarm indicative of a wet diaper condition.

2. The apparatus of claim 1 and wherein said housing is generally button-shaped.

3. The apparatus of claim 1 and wherein said capacitive sensor means is carried on said rear surface of said housing so that it is held firmly against the exterior surface of a diaper when the housing is affixed to the diaper.

4. The apparatus of claim 3 and wherein said first and second conductors of said capacitive sensor means are configured with mutually interleaved fingers to define a parallel plate capacitor configuration.

5. The apparatus of claim 1 and wherein said circuit means comprises means for producing an oscillating voltage signal and applying such signal to said first conductor of said capacitive sensor means, means coupled to said second conductor for detecting the amplitude of the voltage signal capacitively transmitted from said first conductor to said second conductor, means for comparing the detected amplitude to a pre-established threshold amplitude, and means for producing an alarm when the detected amplitude exceeds the pre-established threshold amplitude.

6. The apparatus of claim 1 and wherein said means for removably fixing said housing to the surface of the diaper comprises an adhesive flap sized to be adhered to the diaper with said housing sandwiched between said flap and said diaper.

7. The apparatus of claim 6 and wherein said adhesive flap is formed with a tear-away tab positioned such that said housing can be located in a region of said tab when said housing is sandwiched between said flap and the diaper.

8. The apparatus of claim 1 and wherein said housing is non-adhesively affixed to said diaper.

9. The apparatus of claim 1 and wherein said housing is disposed on an outer surface of said diaper.

10. An apparatus for use with a diaper to detect the occurrence of a wet condition in the diaper and produce an alarm signal in response to such detection, said apparatus comprising:

a housing having a front surface and a rear surface and being sized to contain electronic components and to be affixed to a surface of a diaper;

capacitive sensor means located on said housing and having a first conductor capacitively coupled to a second conductor;

circuit means in said housing for monitoring the electrical capacitance between said first conductor and said second conductor of said capacitive sensor means;

means for producing an electrical signal when the electrical capacitance between said first conductor and said second conductor meets a pre-established criteria;

means responsive to said electrical signal for producing an alarm;

means for removably affixing said housing to the surface of the diaper;

said means for removably fixing said housing to the surface of the diaper comprising an adhesive flap sized to be adhered to the diaper with said housing sandwiched between said flap and said diaper;

said adhesive flap being formed with a tear-away tab positioned such that said housing can be located in a region of said tab when said housing is sandwiched between said flap and the diaper;

said tab having a bulbous portion in the center of said flap and an elongated portion extending outwardly from said bulbous portion toward the edge of said flap, said bulbous portion having a size corresponding to the size of said housing and said housing being located within the bulbous portion when fixed to the diaper, whereby said housing can be removably fixed to the outside surface of a diaper by means of said flap and changing capacitance between the first and second conductors triggers an alarm indicative of a wet diaper condition.

11. The apparatus of claim 10 and wherein said bulbous portion is provided with an opening through which an audible alarm signal can be transmitted from said housing.

12. The apparatus of claim 11 and wherein said elongated portion of said tab extends beyond an edge of said flap to provide a finger that can be grasped to tear the tab away from the flap and thus remove said housing from the diaper for future use.

13. The apparatus of claim 12 and wherein adhesive is provided on the back of said flap only in regions outside of the region defined by said flap.

\* \* \* \* \*